US00PP34416P2

(12) United States Plant Patent
Laymon

(10) Patent No.: US PP34,416 P2
(45) Date of Patent: Jul. 12, 2022

(54) APPLE TREE NAMED 'STARLORD'

(50) Latin Name: *Malus domestica*
Varietal Denomination: 'Starlord'

(71) Applicant: Robert Laymon, Rochester, WA (US)

(72) Inventor: Robert Laymon, Rochester, WA (US)

( * ) Notice: Subject to any disclaimer, the term of this patent is extended or adjusted under 35 U.S.C. 154(b) by 0 days.

(21) Appl. No.: 17/300,766

(22) Filed: Oct. 27, 2021

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875
See application file for complete search history.

*Primary Examiner* — Kent L Bell
(74) *Attorney, Agent, or Firm* — Michelle Bos Legal LLC

(57) ABSTRACT

'Starlord' is a new apple tree selected for its resistance to apple Anthracnose, and for its large, flavorful fruit.

4 Drawing Sheets

Latin name: *Malus domestica.*
Variety denomination: 'Starlord'.

BACKGROUND OF THE VARIETY:

'Starlord' is a new and distinct apple tree (*Malus domestica*) that originated as a chance seedling in a cultivated area at Rochester, Wash. The seedling originated in approximately 2010; its distinct characteristics were first observed by the inventor in 2016. Other apple trees growing nearby included 'Honeycrisp' (U.S. Plant Pat. No. 7,197), which may be a parent of the new variety, but exact parentage is unknown. Plant material of the newly discovered seedling was first propagated by grafting in 2018 at Rochester, Wash. 'Starlord' has since been observed to remain true to type through successive asexually propagated generations.

BRIEF DESCRIPTION OF THE VARIETY

The 'Starlord' apple tree is distinguished by its resistance to apple anthracnose (canker, *Neofabraea malicorticis*), and by its flavorful fruit. 'Starlord' is distinguished from similar variety 'Honeycrisp' by its larger fruit size, longer shelf life, longer harvest window, and one- to two-week earlier bloom time.

BRIEF DESCRIPTION OF THE PHOTOGRAPHS

The accompanying photographs were taken in 2020 at Rochester, Wash. The tree shown is the original 'Starlord' tree grown on its own roots.

DETAILED BOTANICAL DESCRIPTION OF THE VARIETY

Figure 1:
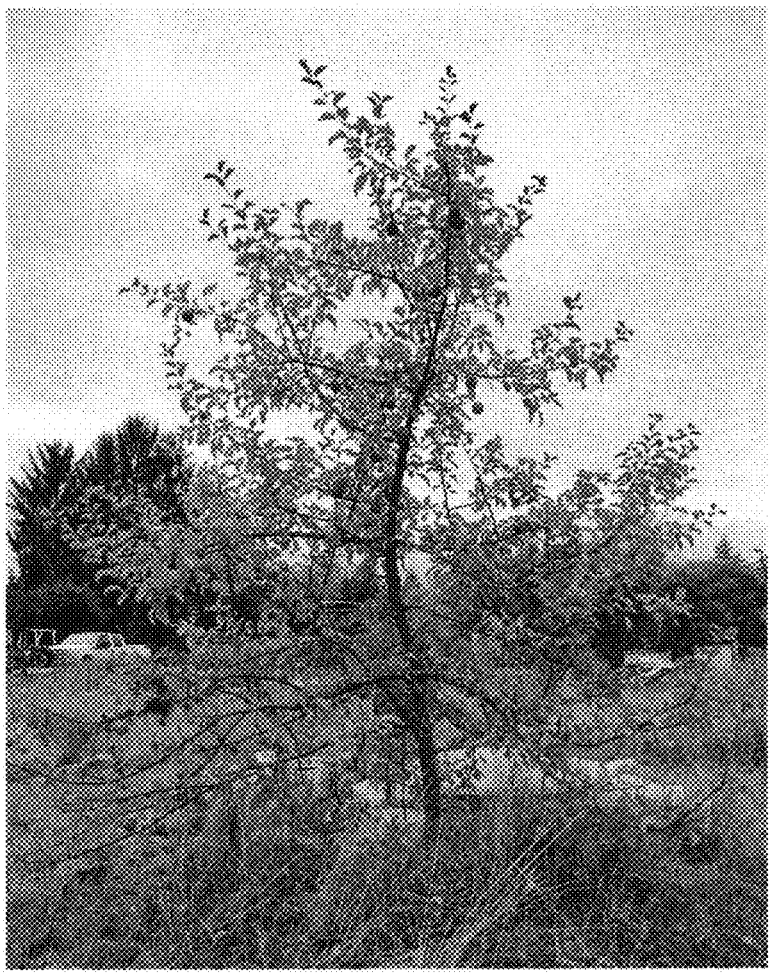
FIG. 1 is a photograph of a 'Starlord' apple tree with leaves and fruit.
Figure 2:
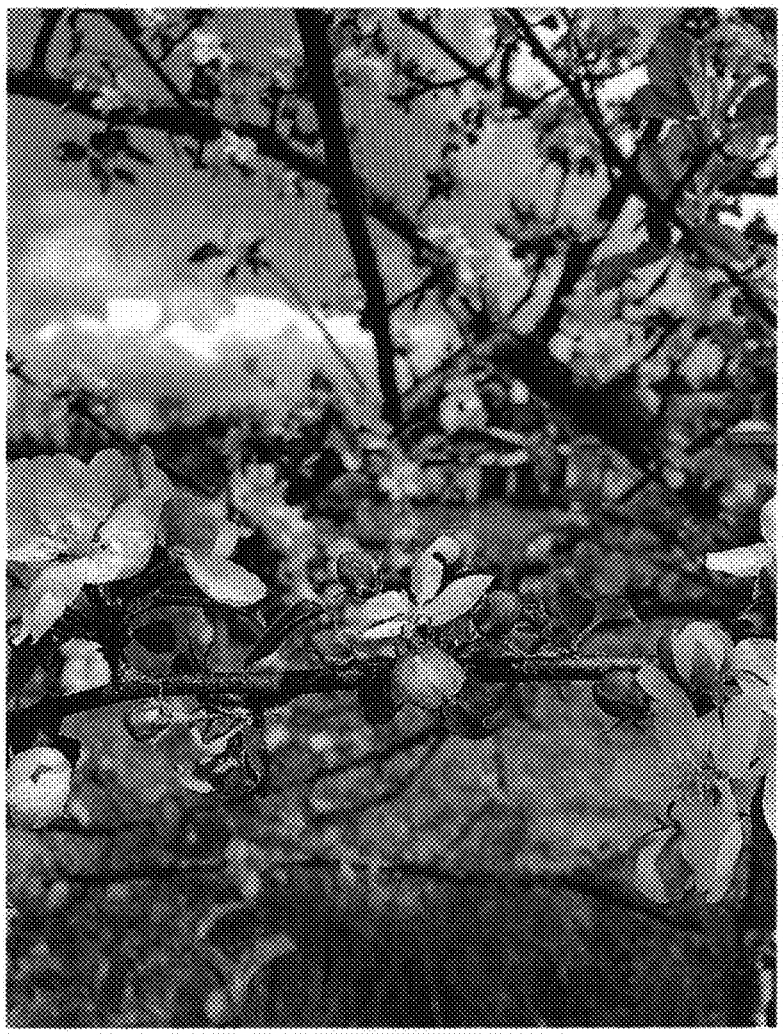
FIG. 2 is a photograph of a flower blossoms and buds on a 'Starlord' apple tree.
Figure 3:
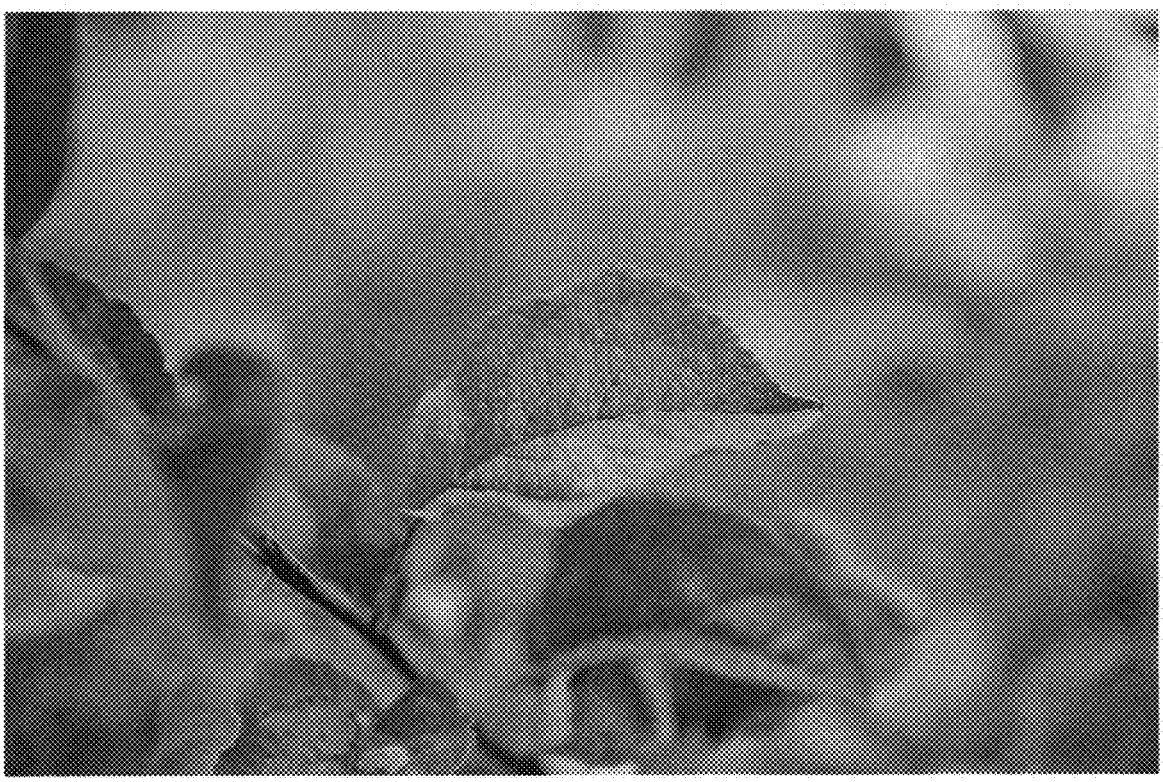
FIG. 3 is a photograph of leaves of a 'Starlord' apple tree.
Figure 4:
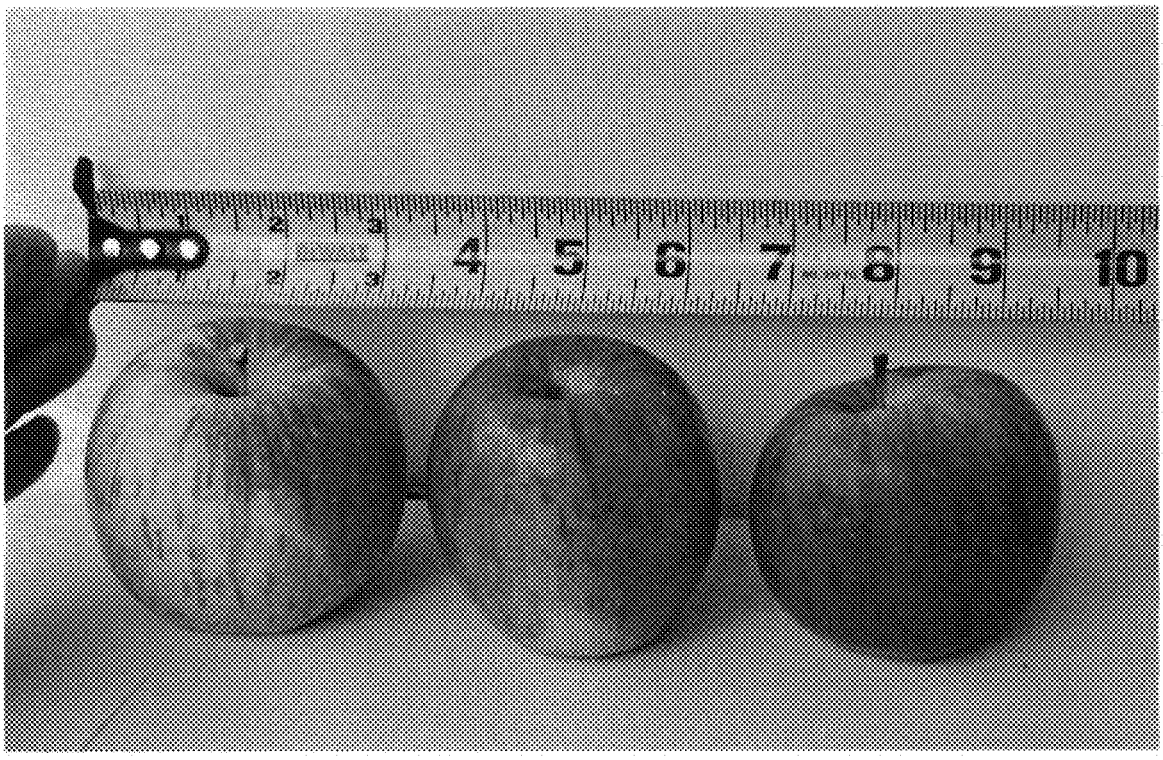
FIG. 4 is a photograph of fruit from a 'Starlord' apple tree.

The following detailed botanical description was recorded at Rochester, Wash. in 2020. The described tree is the original 'Starlord' tree grown on its own roots. All colors are described according to The R.H.S. Colour Chart (Royal Horticultural Society, 5$^{th}$ ed.). The characteristics described will vary somewhat depending upon cultural practices and climatic conditions, and will vary with location and season. Quantified measurements are expressed as an average of a number of measurements taken from the described plant. The measurements of any individual plant or any group of plants of the new variety may vary from the stated average.

Tree:
- *Vigor.*—Moderate.
- *Type.*—Ramified.
- *Habit.*—Spreading.
- *Bearing.*—On shoots.
- *Spread of mature tree.*—5.2 m (unpruned).
- *Height.*—5 m (unpruned).
- *Trunk diameter* (*at* 30 *cm above the graft*).—14 cm.
- *Bark texture.*—Old wood rough, new wood smooth.
- *Bark color.*—Brown N200B.
- *Lenticel length.*—1 cm to 2 cm.
- *Lenticel width.*—2 mm.
- *Lenticel height.*—0.3 mm.
- *Lenticel shape.*—Elongated.
- *Lenticel color.*—Orange-white 159C.
- *Lenticel density.*—15 to 20 per 10 cm$^2$.

Branch (fruiting branches located at around 1 m above the graft union):
- *Length.*—1.8 m (unpruned).
- *Diameter.*—2 cm.
- *Crotch angle.*—80° to 90°.
- *Bark color.*—Grey-brown 199A.
- *Lenticel length.*—4 mm.
- *Lenticel width.*—1 mm.
- *Lenticel height.*—0.2 mm.
- *Lenticel shape.*—Elongated oval.
- *Lenticel color.*—Greyed-yellow 161C.
- *Lenticel density.*—Dense, 20 or more per cm$^2$.

One year old shoot:
- *Length.*—12 cm.
- *Diameter.*—5 mm.
- *Color.*—Brown 200A.

*Pubescence*.—None.
*Internode length*.—6 cm.
*Lenticel length*.—1 mm.
*Lenticel width*.—1 mm.
*Lenticel height*.—0.2 mm.
*Lenticel shape*.—Round.
*Lenticel color*.—Greyed-yellow 161C.
*Lenticel density*.—Dense, about 20 per $cm^2$.

Flower buds at balloon stage:
*Quantity per spur*.—4 to 6.
*Bud shape*.—Round.
*Apex shape*.—Rounded.
*Texture*.—Pubescent.
*Length*.—10 mm.
*Diameter*.—20 mm.
*Color*.—Tightly closed red 53C; nearly open red 54A.

Flowers:
*Diameter of fully open flower*.—20 mm.
*Depth of fully open flower*.—6 mm.
*Relative position of petal margin*.—Touching.
*Number per cluster*.—4 to 6.
*Date of first bloom* (2020).—April 17.
*Date of full bloom* (2020).—April 24.
*Pollination requirement*.—Unknown, possibly 'Honeycrisp', 'Jonathan' (not patented) or 'Williams Pride' (also known as 'Co-op 32', U.S. Plant Pat. No. 9,881).
*Fragrance*.—Mild.

Petals:
*Number per flower*.—5.
*Petal shape*.—Ovate.
*Length*.—23 mm.
*Width*.—19 mm.
*Apex shape*.—Obtuse.
*Base shape*.—Rounded to slightly cordate.
*Texture*.—Smooth to rugulose.
*Margin*.—Entire; mildly undulate.
*Color of upper surface*.—White NN155D with trace of red-purple 64C.
*Color of lower surface*.—White NN155D with trace of red-purple 64C.

Pistils:
*Length*.—9 mm.
*Quantity*.—About 4 to 6 per flower.
*Color*.—Green-white 157C with yellow-green 144C near stigma.

Stigma:
*Diameter*.—2 mm.
*Color*.—Yellow-green 144C.

Style:
*Diameter*.—0.7 mm.
*Color*.—Yellow-green 144C.

Ovary:
*Length*.—3.8 mm.
*Diameter*.—1.3 mm.
*Color*.—Yellow-green 144C.

Stamens:
*Quantity*.—20.
*Filament length*.—8 mm to 12 mm.
*Anther diameter*.—1 mm.
*Anther color*.—Yellow 10B.
*Pollen presence*.—Scarce.
*Pollen color*.—Yellow 10B.

Pedicel:
*Length*.—15 mm to 25 mm.
*Diameter*.—1.5 mm.
*Color*.—Yellow-green 144A with faint anthocyanin coloration greyed-red 178A.
*Pubescence*.—Present.

Sepals:
*Quantity*.—5.
*Color of upper surface*.—Yellow-green 144A.
*Color of lower surface*.—Yellow-green 144A.
*Length*.—10 mm.
*Width*.—3 mm at base.
*Sepal shape*.—Lanceolate.
*Apex shape*.—Mucronate.
*Margin*.—Entire.
*Texture*.—Both surfaces mildly pubescent.

Leaves:
*Shape*.—Broadly elliptic.
*Length*.—100 mm.
*Width*.—76 mm.
*Leaf margin*.—Serrate.
*Apex*.—Acuminate.
*Base shape*.—Rounded, equilateral.
*Texture of upper surface*.—Smooth to mildly rugulose.
*Texture of lower surface*.—Smooth with prominent veins.
*Color of upper surface*.—Green 137B.
*Color of lower surface*.—Green 137B.
*Attitude in relation to shoot*.—Upward.

Petiole:
*Length*.—29 mm.
*Diameter*.—2 mm.
*Color*.—Light green 144C with anthocyanin coloration greyed-red 178A.

Fruit:
*Quantity per cluster*.—1 to 2.
*Diameter*.—75 mm.
*Height*.—80 mm.
*Weight*.—Varies; average 240 g.
*General shape in profile*.—Globose to globose conical.
*Position of maximum diameter*.—Upper middle.
*Ribbing*.—Weak.
*Crowning at calyx end*.—Weak.
*Bloom of skin*.—Weak.
*Greasiness of skin*.—Weak.
*Background color of skin*.—Yellow-orange 20B.
*Over color of skin*.—Red 45A.
*Amount of over color*.—Usually about 50% to 75%.
*Intensity of over color*.—Medium.
*Pattern of over color*.—Stripe and flush.
*Russet around stalk cavity*.—Absent or weak.
*Russet on cheeks*.—Absent or weak.
*Russet around eye basin*.—Absent or weak.
*Stalk length*.—24 mm.
*Stalk diameter*.—2 mm.
*Stalk color*.—Yellow-green 152D.
*Depth of stalk cavity*.—5 mm.
*Width of stalk cavity*.—25 mm.
*Depth of eye basin*.—16 mm.
*Width of eye basin*.—21 mm.
*Aperture of eye*.—Closed.
*Flesh firmness*.—Moderate.
*Flesh texture*.—Fine, crisp.
*Flesh flavor*.—Balanced acid and sugar; more intense flavor than 'Honeycrisp'.

*Juiciness*.—Moderate.
*Aroma*.—Similar to 'Honeycrisp'.
*Flesh color*.—White NN155B.
*Locule quantity*.—5.
*Locule width*.—4 mm to 5 mm.
*Locule aperature*.—Moderately open.

Seeds:
*Quantity per fruit*.—3 to 4.
*Length*.—9 mm.
*Width*.—4 mm.
*Shape*.—Oval-oblong.
*Color*.—Black 202A.

Disease resistance: Somewhat resistant to canker (apple anthracnose, *Neofabraea malicorticis*).
Harvest date range: September 1 to October 31 (2020 growing season).
Harvest yield: About 210 pounds.
Eating quality: Excellent fresh eating.
Fruit storage characteristics: Stores well in standard storage conditions.

The invention claimed is:

1. A new and distinct apple tree named 'Starlord' substantially as described and illustrated herein.

* * * * *